(12) United States Patent
Radman

(10) Patent No.: US 11,484,698 B2
(45) Date of Patent: Nov. 1, 2022

(54) CIRCULATORY SUPPORT DEVICE

(71) Applicant: Boston Scientific Scimed Inc., Maple Grove, MN (US)

(72) Inventor: Lloyd Radman, Blaine, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 28 days.

(21) Appl. No.: 16/720,620

(22) Filed: Dec. 19, 2019

(65) Prior Publication Data
US 2021/0008264 A1    Jan. 14, 2021

Related U.S. Application Data

(60) Provisional application No. 62/872,127, filed on Jul. 9, 2019.

(51) Int. Cl.
| | |
|---|---|
| *A61M 60/135* | (2021.01) |
| *A61M 60/40* | (2021.01) |
| *A61M 60/50* | (2021.01) |
| *A61M 60/205* | (2021.01) |
| *A61M 60/857* | (2021.01) |

(52) U.S. Cl.
CPC ........ *A61M 60/135* (2021.01); *A61M 60/205* (2021.01); *A61M 60/40* (2021.01); *A61M 60/50* (2021.01); *A61M 60/857* (2021.01); *A61M 2205/103* (2013.01)

(58) Field of Classification Search
None
See application file for complete search history.

(56) References Cited

U.S. PATENT DOCUMENTS

| | | | |
|---|---|---|---|
| 5,911,685 A | * | 6/1999 | Siess ...................... H02K 5/132 600/16 |
| 6,790,171 B1 | | 9/2004 | Gruendeman et al. |
| 7,544,160 B2 | * | 6/2009 | Gross .................... A61F 2/2469 600/16 |
| 7,780,646 B2 | * | 8/2010 | Farnholtz .......... A61M 25/0147 604/525 |

(Continued)

FOREIGN PATENT DOCUMENTS

| | | |
|---|---|---|
| EP | 3108909 A1 | 12/2016 |
| JP | 2018-535727 A | 12/2018 |

(Continued)

OTHER PUBLICATIONS

International Search Report and Written Opinion received for PCT Patent Application No. PCT/US2019/067420, dated Apr. 2, 2020, 14 pages.

(Continued)

*Primary Examiner* — Carl H Layno
*Assistant Examiner* — Manolis Pahakis
(74) *Attorney, Agent, or Firm* — Faegre Drinker Biddle & Reath LLP

(57) ABSTRACT

A circulatory support device includes a flexible cannula having a fluid outlet at a proximal end; and a pump assembly disposed at a distal end of the flexible cannula. The pump assembly includes a pump housing having a fluid inlet defined therein; a motor disposed within a distal end of the housing; and an impeller, driven to rotate by the motor, and configured to push blood toward the fluid outlet.

16 Claims, 6 Drawing Sheets

(56) References Cited

U.S. PATENT DOCUMENTS

| | | | | |
|---|---|---|---|---|
| 7,828,790 | B2* | 11/2010 | Griffin | A61M 25/005 604/525 |
| 8,177,703 | B2* | 5/2012 | Smith | A61M 60/422 600/16 |
| 8,690,749 | B1* | 4/2014 | Nunez | A61M 60/205 600/16 |
| 9,539,378 | B2* | 1/2017 | Tuseth | A61B 17/3478 |
| 9,907,890 | B2* | 3/2018 | Muller | A61M 60/818 |
| 10,722,631 | B2* | 7/2020 | Salahieh | A61M 60/857 |
| 10,881,770 | B2* | 1/2021 | Tuval | F04D 29/247 |
| 11,033,727 | B2* | 6/2021 | Tuval | A61M 60/205 |
| 11,039,915 | B2* | 6/2021 | Tuval | A61F 2/06 |
| 11,116,959 | B2* | 9/2021 | Alexander | F04D 13/028 |
| 11,185,677 | B2* | 11/2021 | Salahieh | A61M 60/824 |
| 11,185,678 | B2* | 11/2021 | Smith | A61M 60/82 |
| 2002/0026944 | A1 | 3/2002 | Aboul-Hosn et al. | |
| 2003/0187322 | A1* | 10/2003 | Siess | A61M 60/419 600/16 |
| 2003/0233143 | A1* | 12/2003 | Gharib | A61M 60/00 623/3.1 |
| 2005/0049696 | A1* | 3/2005 | Siess | A61F 2/2433 623/2.11 |
| 2006/0036127 | A1* | 2/2006 | Delgado, III | A61M 60/135 600/16 |
| 2007/0156006 | A1* | 7/2007 | Smith | A61M 60/422 600/16 |
| 2008/0114339 | A1* | 5/2008 | McBride | A61M 60/148 604/891.1 |
| 2011/0152999 | A1* | 6/2011 | Hastings | A61M 60/40 623/1.15 |
| 2013/0053623 | A1* | 2/2013 | Evans | A61M 60/825 600/16 |
| 2013/0060077 | A1* | 3/2013 | Liebing | F04D 29/181 600/16 |
| 2013/0303831 | A1* | 11/2013 | Evans | A61M 1/101 600/16 |
| 2014/0128659 | A1* | 5/2014 | Heuring | A61M 60/205 600/16 |
| 2014/0255176 | A1* | 9/2014 | Bredenbreuker | F04D 15/0005 415/208.1 |
| 2017/0100527 | A1* | 4/2017 | Schwammenthal | A61M 60/857 |
| 2017/0340789 | A1 | 11/2017 | Bonde et al. | |
| 2018/0126130 | A1* | 5/2018 | Nitzan | A61M 60/833 |
| 2018/0169313 | A1* | 6/2018 | Schwammenthal | A61M 60/40 |
| 2020/0405926 | A1* | 12/2020 | Alexander | A61M 60/408 |
| 2021/0346678 | A1* | 11/2021 | Baumbach | G16H 40/67 |

FOREIGN PATENT DOCUMENTS

| | | |
|---|---|---|
| WO | 2009/073037 A1 | 6/2009 |
| WO | 2017/162618 A1 | 9/2017 |
| WO | 2018/226991 A1 | 12/2018 |

OTHER PUBLICATIONS

International Preliminary Reporton Patentability received for PCT Patent Application No. PCT/US2019/067420, dated Jul. 1, 2021, 8 pages.

* cited by examiner

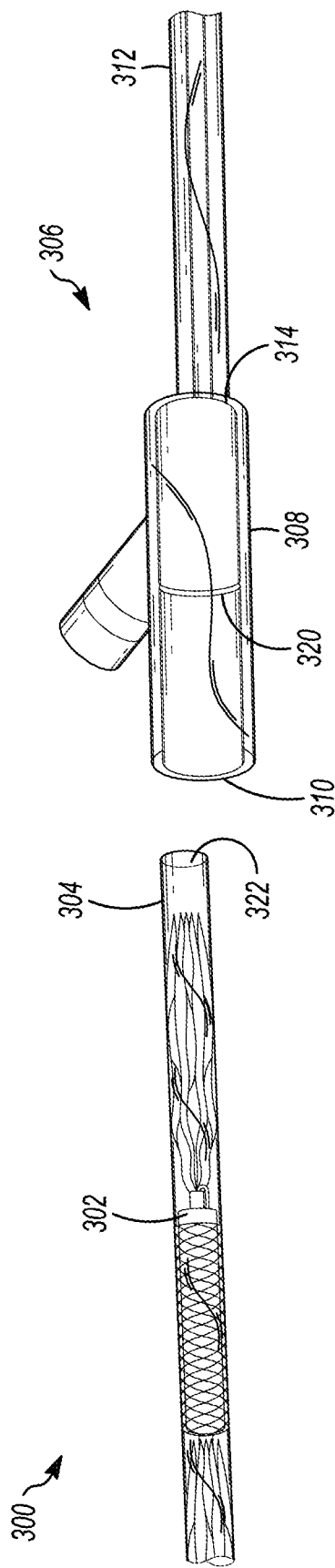
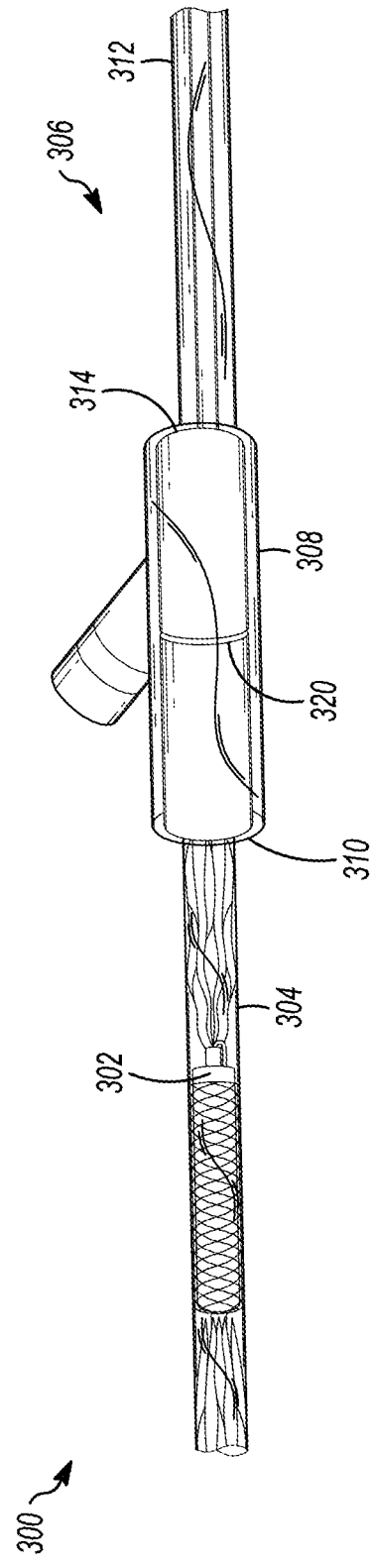
FIG. 3A
FIG. 3B

CIRCULATORY SUPPORT DEVICE

CROSS REFERENCE TO RELATED APPLICATION

This application claims priority to Provisional Application No. 62/782,127, filed Dec. 19, 2018, which is herein incorporated by reference in its entirety.

TECHNICAL FIELD

The present disclosure relates to percutaneous circulatory support devices. More specifically, the disclosure relates to a circulatory support device having a flexible cannula and a reverse flow direction.

BACKGROUND

Circulatory support devices may be disposed through a valve opening such as, for example, an aortic valve. In some cases, the size of the device may cause stress on the valve when the valve closes over the device. In the case of a motor failure, typical circulatory support devices may cause pressure differences between a left ventricle and an aorta. Additionally, typical circulatory support devices are prone to moving, resulting in a need for repositioning before treatment is continued.

SUMMARY

In an Example 1, a circulatory support device comprising: a flexible cannula having a fluid outlet at a proximal end; and a pump assembly disposed at a distal end of the flexible cannula, the pump assembly comprising: a pump housing having a fluid inlet defined therein; a motor disposed within a distal end of the housing; and an impeller, driven to rotate by the motor, and configured to push blood toward the fluid outlet.

In an Example 2, the circulatory support device of Example 1, further comprising a mesh skirt at least partially surrounding the pump housing, adjacent the fluid inlet.

In an Example 3, the circulatory support device of either of Examples 1 or 2, further comprising an expandable cage coupled to the distal end of the pump housing.

In an Example 4, the circulatory support device of any of Examples 1-3, further comprising an expandable cage coupled to the proximal end of the flexible cannula.

In an Example 5, the circulatory support device of any of Examples 1-3, further comprising: a first expandable cage coupled to the distal end of the pump housing and configured to be disposed within a left ventricle of a subject; and a second expandable cage coupled to the proximal end of the flexible cannula and configured to be disposed within the aorta.

In an Example 6, the circulatory support device of any of Examples 1-5, further comprising a helical tube coupled to a proximal end of the pump housing and extending through at least a portion of the flexible cannula, wherein one or more conductors are disposed within the helical tube.

In an Example 7, the circulatory support device of any of Examples 1-6, wherein at least a portion of the flexible cannula is configured to be disposed through an aortic valve opening and is configured to be compressible such that the aortic valve can close on the at least the portion of the flexible cannula.

In an Example 8, a circulatory support device comprising: a flexible cannula having a fluid outlet at a proximal end; a pump assembly disposed at a distal end of the flexible cannula, the pump assembly comprising: a pump housing having a fluid inlet defined therein; a motor disposed within a distal end of the housing; and an impeller, driven to rotate by the motor, and configured to push blood toward the fluid outlet; and a first expandable cage coupled to a distal end of the pump housing; and a second expandable cage coupled to the proximal end of the flexible cannula.

In an Example 9, the circulatory support device of Example 8, further comprising a mesh skirt at least partially surrounding the pump housing, adjacent the fluid inlet.

In an Example 10, the circulatory support device of either of Examples 8 or 9, wherein the fluid inlet is disposed between the flexible cannula and the motor.

In an Example 11, the circulatory support device of any of Examples 8-10, wherein the first expandable cage is configured to be disposed in a left ventricle of a subject.

In an Example 12, the circulatory support device of any of Examples 8-11, wherein the second expandable cage is configured to be disposed in an aorta of a subject.

In an Example 13, the circulatory support device of any of Examples 8-12, further comprising a helical tube coupled to a proximal end of the pump housing and extending through at least a portion of the flexible cannula, wherein one or more conductors are disposed within the helical tube.

In an Example 14, the circulatory support device of Example 13, wherein the one or more conductors are configured to operably couple the motor to a control unit and extend from a distal end of the helical tube, along an outside of the pump housing, and into a distal end of the pump housing.

In an Example 15, the circulatory support device of any of Examples 8-14, wherein at least a portion of the flexible cannula is configured to be disposed through an aortic valve opening and is configured to be compressible such that the aortic valve can close on the at least the portion of the flexible cannula.

In an Example 16, a circulatory support device comprising: a flexible cannula having a fluid outlet at a proximal end; and a pump assembly disposed at a distal end of the flexible cannula, the pump assembly comprising: a pump housing having a fluid inlet defined therein; a motor disposed within a distal end of the housing; and an impeller, driven to rotate by the motor, and configured to push blood toward the fluid outlet.

In an Example 17, the circulatory support device of Example 16, further comprising a mesh skirt at least partially surrounding the pump housing, adjacent the fluid inlet.

In an Example 18, the circulatory support device of Example 16, further comprising an expandable cage coupled to the distal end of the pump housing.

In an Example 19, the circulatory support device of Example 16, further comprising an expandable cage coupled to the proximal end of the flexible cannula.

In an Example 20, the circulatory support device of Example 16, further comprising: a first expandable cage coupled to the distal end of the pump housing and configured to be disposed within a left ventricle of a subject; and a second expandable cage coupled to the proximal end of the flexible cannula and configured to be disposed within the aorta.

In an Example 21, the circulatory support device of Example 16, further comprising a helical tube coupled to a proximal end of the pump housing and extending through at least a portion of the flexible cannula, wherein one or more conductors are disposed within the helical tube.

In an Example 22, the circulatory support device of Example 16, wherein at least a portion of the flexible cannula is configured to be disposed through an aortic valve opening and is configured to be compressible such that the aortic valve can close on the at least the portion of the flexible cannula.

In an Example 23, a circulatory support device comprising: a flexible cannula having a fluid outlet at a proximal end; a pump assembly disposed at a distal end of the flexible cannula, the pump assembly comprising: a pump housing having a fluid inlet defined therein; a motor disposed within a distal end of the housing; and an impeller, driven to rotate by the motor, and configured to push blood toward the fluid outlet; and a first expandable cage coupled to a distal end of the pump housing; and a second expandable cage coupled to the proximal end of the flexible cannula.

In an Example 24, the circulatory support device of Example 23, further comprising a mesh skirt at least partially surrounding the pump housing, adjacent the fluid inlet.

In an Example 25, the circulatory support device of Example 23, wherein the fluid inlet is disposed between the flexible cannula and the motor.

In an Example 26, the circulatory support device of Example 23, wherein the first expandable cage is configured to be disposed in a left ventricle of a subject.

In an Example 27, the circulatory support device of Example 23, wherein the second expandable cage is configured to be disposed in an aorta of a subject.

In an Example 28, the circulatory support device of Example 23, further comprising a helical tube coupled to a proximal end of the pump housing and extending through at least a portion of the flexible cannula, wherein one or more conductors are disposed within the helical tube.

In an Example 29, the circulatory support device of Example 28, wherein the one or more conductors are configured to operably couple the motor to a control unit and extend from a distal end of the helical tube, along an outside of the pump housing, and into a distal end of the pump housing.

In an Example 30, the circulatory support device of Example 23, wherein at least a portion of the flexible cannula is configured to be disposed through an aortic valve opening and is configured to be compressible such that the aortic valve can close on the at least the portion of the flexible cannula.

In an Example 31, a method of deploying a circulatory support device, the circulatory support device comprising a flexible cannula having a fluid outlet at a proximal end; a helical tube coupled to a proximal end of the pump housing and extending through at least a portion of the flexible cannula; a pump assembly disposed at a distal end of the flexible cannula, the pump assembly comprising a pump housing having a fluid inlet defined therein; a motor disposed within a distal end of the housing; and an impeller, driven to rotate by the motor, and configured to push blood toward the fluid outlet; and an expandable cage coupled to the distal end of the pump housing, the method comprising: navigating a delivery sheath to a deployment location, the delivery sheath comprising (1) an insertion manifold having a proximal opening and a distal opening, and (2) a delivery shaft extending from the distal opening; navigating the circulatory support device to the delivery sheath, wherein the circulatory support device is disposed within a protector tube; inserting the circulatory support device and protector tube into the proximal opening of the insertion manifold, wherein the insertion manifold includes a stop surface disposed therein and configured to engage a distal edge of the protector tube, thereby preventing the protector tube from being pushed into the delivery shaft; pushing the circulatory support device into the delivery shaft, wherein the protector tube is prevented from entering the delivery shaft by the stop surface; and pushing the circulatory support device out of a distal end of the delivery shaft, wherein, upon exiting the delivery shaft, an expandable cage expands and engages a cage location, thereby securing the circulatory support device in place.

In an Example 32, the method of Example 31, wherein navigating the delivery sheath to the deployment location comprises passing a guidewire through the delivery sheath and tracking at least one of the guidewire and the delivery sheath during navigation.

In an Example 33, the method of Example 31, wherein navigating the delivery sheath to the deployment location comprises positioning the distal end of the delivery shaft adjacent the cage location.

In an Example 34, the method of Example 31, wherein pushing the circulatory support device into the delivery shaft comprises pushing on the helical tube.

In an Example 35, the method of Example 31, wherein deploying the circulatory support device comprises positioning the circulatory support device in a deployment location without inserting a guidewire through the circulatory support device.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIGS. 3A-3D depict an illustrative circulatory support device delivery system, in different stages of a process of deploying a circulatory support device, in accordance with embodiments of the subject matter disclosed herein.

Figure 1:
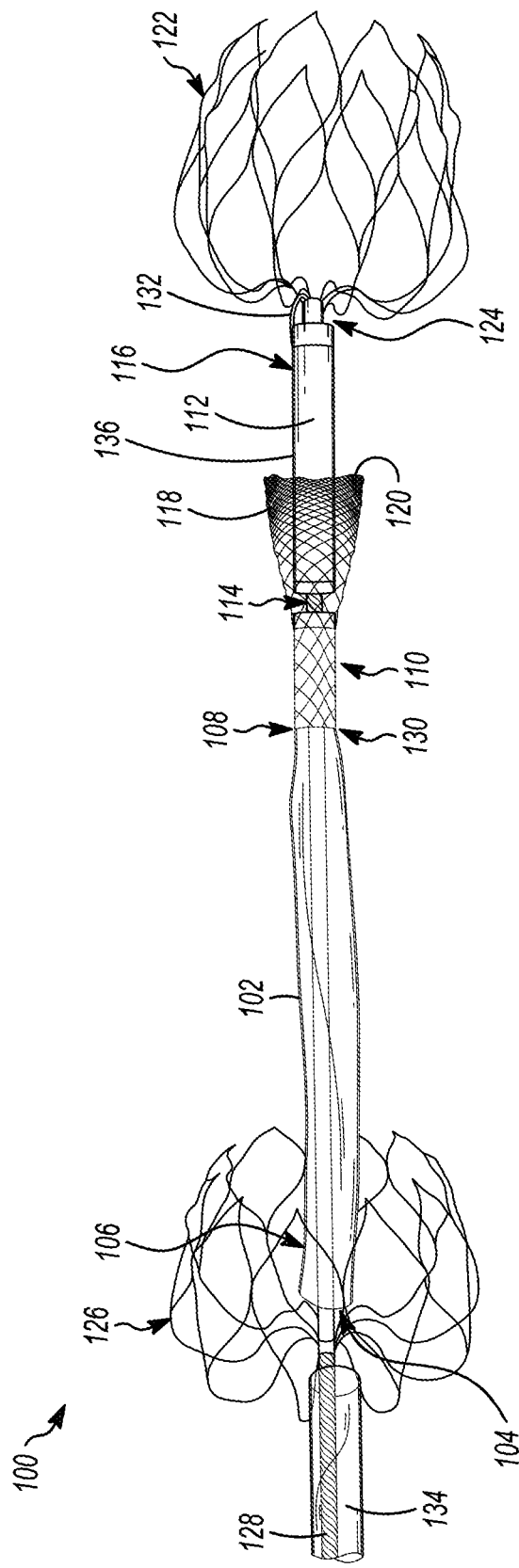
FIG. 1 depicts a side view of an illustrative percutaneous mechanical circulatory support device, in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Embodiments of the subject matter disclosed herein include bearing designs that may facilitate reducing heat formation by using lubrication, and reducing mechanical blood damage by preventing ingress of blood onto bearing surfaces. Bearing designs that include concave depressions and closed cavities facilitate preventing blood ingress onto bearing surfaces. Lubrication may be used to provide a fluid film at bearing surfaces to minimize wear. According to embodiments, any number of different types of lubricants may be used such as, for example, hydrophobic, water-insoluble lubricants (e.g., perfluoropolyether or poly-alpha-olefins classes of synthetic lubricants) may be used.

FIG. 1 depicts a side view of an illustrative percutaneous mechanical circulatory support device 100, in accordance with embodiments of the subject matter disclosed herein. According to embodiments, the circulatory support device 100 may be a ventricular assist device configured to pump blood from a left ventricle of a subject into the subject's aorta. In embodiments, the circulatory support device 100 may be used to facilitate pumping blood from some other aspect of the subject's vasculature into an adjacent portion of the vasculature.

As shown in FIG. 1, the circulatory support device 100 includes a flexible cannula 102 having a fluid outlet 104 at a proximal end 106 and coupled, at a distal end 108, to a pump assembly 110. According to embodiments, the flexible cannula 102, or at least a portion thereof, may be configured to be disposed through a heart valve opening such as, for example, an aortic valve opening. In embodiments, the flexible cannula 102 may be configured to be compressible such that the heart valve can close on the cannula (or the portion thereof) without causing leaking through the valve. In this manner, for example, embodiments of the subject matter may be configured to prevent (or at least mitigate) pressure differences between the left ventricle and the aorta in the case of a motor failure of the device 100.

As is further shown in FIG. 1, the pump assembly 110 includes a pump housing 112 having a fluid inlet 114 defined therein. A motor (not shown in FIG. 1) may be disposed within a distal portion 116 of the housing 112. The motor may be configured to drive an impeller (not shown in FIG. 1), disposed proximal to the motor, which may be configured to push blood toward the fluid outlet 104. In embodiments, the circulatory support device 100 includes a mesh skirt 118 at least partially surrounding the pump housing 112, adjacent the fluid inlet 114. The mesh skirt 118 may be configured to facilitate blood flow into the fluid inlet 114 and/or to prevent larger particles from entering the fluid inlet 114. As shown, the mesh skirt 118 may be configured in a conical shape, with an opening 120 facing distally.

A first expandable cage 122 may be coupled to the distal end 124 of the pump housing 112. In embodiments, the first expandable cage 122 may be configured to be disposed in a first portion of a subject's vasculature such as, for example, within a left ventricle of a subject. As shown in FIG. 1, a second expandable cage 126 may be coupled to (or adjacent) the proximal end 106 of the flexible cannula 102. In embodiments, the second expandable cage 126 may be configured to be disposed within a second portion of the subject's vasculature such as, for example, the subject's aorta. In this manner, for example, the circulatory support device 100 may be used as a ventricular assist device, having an impeller disposed in the ventricle, pumping blood to a blood outlet disposed in the aorta. The first and/or second expandable cage 122, 126 may facilitate keeping the device 100 in place, even during patient movement. According to embodiments, use of the design described herein for pumping the blood from the ventricle into the aorta, with an impeller disposed in the ventricle may facilitate allowing the aortic valve to close on the flexible cannula, thereby preventing back flow while simulating pumping of the heart.

As is further shown in FIG. 1, the circulatory support device 100 includes a helical tube 128 coupled to a proximal end 130 of the pump housing 112 and extending through at least a portion of the flexible cannula 102, wherein one or more conductors 132 are disposed within the helical tube 128. That is, for example, the helical tube 128 provides a conduit therein for enclosing control and/or power conductors extending from a control unit to the motor, where the conductors facilitate controlling the motor. The helical tube 128 may be enclosed, in embodiments, by a catheter sleeve 134. As is further shown, in embodiments, the one or more conductors 132 may be configured to extend from a distal end of the helical tube 128, along an outside of the pump housing 112, and into a distal end 124 of the pump housing 112. A housing sleeve 136 may be disposed over at least a portion of the one or more conductors 132 for protection.

The illustrative circulatory support device 100 shown in FIG. 1 is not intended to suggest any limitation as to the scope of use or functionality of embodiments of the present disclosure. The illustrative circulatory support device 100 also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
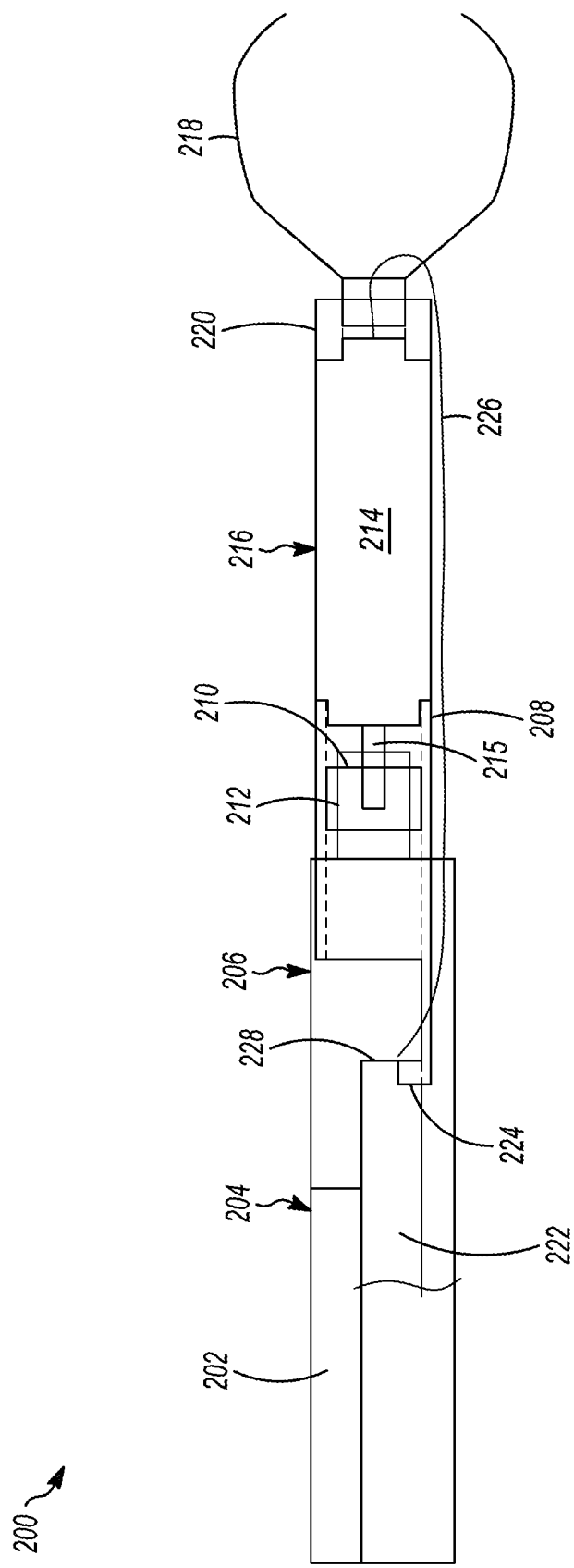
FIG. 2 depicts a cross-sectional side view of an illustrative circulatory support device, in accordance with embodiments of the subject matter disclosed herein.

FIG. 2 depicts a cross-sectional side view of an illustrative circulatory support device 200, in accordance with embodiments of the subject matter disclosed herein. According to embodiments, the circulatory support device 200 may be, or be similar to, the circulatory support device 100 depicted in FIG. 1. As shown in FIG. 2, the circulatory support device 200 includes a flexible cannula 202 having a fluid outlet (not shown in FIG. 2) at a proximal end thereof and coupled, at a distal end 204, to a pump assembly 206. As explained above, with regard to FIG. 1, the flexible cannula 202, or at least a portion thereof, may be configured to be disposed through a heart valve opening such as, for example, an aortic valve opening. In embodiments, the flexible cannula 202 may be configured to be compressible such that the heart valve can close on the cannula (or the portion thereof) without causing leaking through the valve. In this manner, for example, embodiments of the subject matter may be configured to prevent (or at least mitigate) pressure differences between the left ventricle and the aorta in the case of a motor failure of the device 200.

As is further shown in FIG. 2, the pump assembly 206 includes a pump housing 208 having a fluid inlet 210 defined therein. According to embodiments, the fluid inlet 210 may be disposed adjacent an impeller 212 that is also disposed within the pump housing 208. A motor 214 may be disposed within a distal portion 216 of the housing 208. The motor 214 may be configured to drive the impeller 212, via a drive shaft 215, and the impeller 212 and drive shaft 215 may be disposed proximal to the motor 214, which may be configured to push fluid (e.g., blood) toward the fluid outlet. In embodiments, the distal portion 216 of the housing 208 may be laser welded to the motor 214. In embodiments, the circulatory support device 200 includes a mesh skirt (such as, for example, the mesh skirt 118 depicted in FIG. 1) at least partially surrounding the pump housing 208, adjacent the fluid inlet 210. The mesh skirt 118 may be configured to facilitate blood flow into the fluid inlet 210 and/or to prevent larger particles from entering the fluid inlet 210.

An expandable cage 218 may be coupled to the distal end 220 of the pump housing 208. In embodiments, the expandable cage 218 may be configured to be disposed in a first portion of a subject's vasculature such as, for example, within a left ventricle of a subject. Although not shown in FIG. 2, as shown in FIG. 1, a second expandable cage may be coupled to (or adjacent) the proximal end of the flexible cannula 202. In embodiments, the second expandable cage may be configured to be disposed within a second portion of the subject's vasculature such as, for example, the subject's aorta. As is further shown in FIG. 2, the circulatory support device 200 includes a helical tube 222 coupled to a proximal end 224 of the pump housing 208 and extending through at least a portion of the flexible cannula 202, where one or more conductors 226 are disposed within the helical tube 222. According to embodiments, the proximal end 224 of the pump housing 208 may be crimped onto the distal end 228 of the helical tube 222, the two may be laser welded together. As is further shown, in embodiments, the one or more conductors 226 may be configured to extend from a distal end 228 of the helical tube 222, along an outside of the pump housing 208, and into the distal end 220 of the pump housing 208. A housing sleeve (not shown) may be disposed over at least a portion of the one or more conductors 226 for protection.

The illustrative circulatory support device 200 shown in FIG. 2 is not intended to suggest any limitation as to the scope of use or functionality of embodiments of the present disclosure. The illustrative circulatory support device 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Embodiments of the circulatory support device disclosed herein may be configured to be deployed without having to pass a guide wire through the housing of the circulatory support device, in contrast to typical circulatory support device delivery processes. Typically, a guide wire is disposed through the housing of a circulatory support device and the guide wire itself is tracked during delivery. For example, in many typical systems, the guide wire is loaded into the circulatory support device outlet, passed around the impeller and exits the fluid inlet of the device. In many instances, having the guide wire bent around and disposed through the circulatory support device may cause drag during delivery, scraping of the Teflon on the guide wire, and/or the like.

Embodiments of the subject matter disclosed herein may mitigate these issues by allowing a clinician to position and track the circulatory support device without routing a guidewire through the device (e.g., without routing the guidewire through the inlet and outlet of the device). That is, in embodiments, the guidewire is tracked to the left ventricle and, once positioned, the delivery sheath is tracked over the guidewire. Once the delivery sheath is in position, the guidewire is removed. Then, the circulatory device is pushed into the delivery sheath and tracked to position. The deployment process of circulatory support devices in accordance with embodiments of the subject matter disclosed herein may be simpler than typical deployment processes, may reduce drag during positioning, and may reduce the risk of damaging the device and/or the guidewire during deployment.

FIGS. 3A-3D depict an illustrative circulatory support device delivery system 300, in different stages of a process of deploying a circulatory support device 302, in accordance with embodiments of the subject matter disclosed herein. According to embodiments, the illustrative circulatory support device 302 may be, or be similar to, the circulatory support device 100 depicted in FIG. 1 and/or the circulatory support device 200 depicted in FIG. 2.

As shown in FIG. 3A, the circulatory support device system 300 includes a circulatory support device 302 that is, initially, disposed in a circulatory support device protector tube 304, and a delivery sheath 306. The delivery sheath 306 may include an insertion manifold 308 having a proximal opening 310 and a delivery shaft 312 extending from a distal opening 314 of the insertion manifold 308. The delivery sheath 306 may be configured to be positioned, using a guidewire inserted therethrough, such that a distal end 316 of the delivery shaft 312 is disposed adjacent a deployment location. In embodiments, the delivery sheath may be trackable by a tracking system and may include any number of features configured to facilitate its identification and tracking within the body of a subject. In embodiments, the delivery sheath is navigated (e.g., by tracking the delivery sheath 306 and/or guidewire) to a deployment location. At the deployment location, the distal end 316 of the delivery sheath 306 may be positioned at a first cage location—that is, a location at which a first expandable cage 318 is to be disposed (e.g., in the left ventricle). The circulatory support device 302 and protector tube 304 may be configured to be inserted into the subject's vasculature and navigated to the delivery sheath 306.

The circulatory support device 302 and protector tube 304 may be configured to be inserted into the proximal opening 310 of the insertion manifold 308. The insertion manifold 308 may include a stop surface 320 configured to engage a distal edge 322 of the protector tube 304, thereby preventing the protector tube 304 from passing through the insertion manifold 308 into the delivery shaft 312. According to embodiments, the delivery sheath 306 may include a tapered proximal end 308 configured to facilitate reception of the device 302. In operation, as shown in FIG. 3B, the circulatory support device 302 and protector tube 304 may be inserted into the insertion manifold 308 by pushing on the helical tube of the device 302. After the distal edge 322 of the protector tube 304 engages the stop surface 320, the clinician may push on the helical tube to push the device 302 into the delivery shaft 312, leaving the protector tube 304 behind.

Figure 3C:
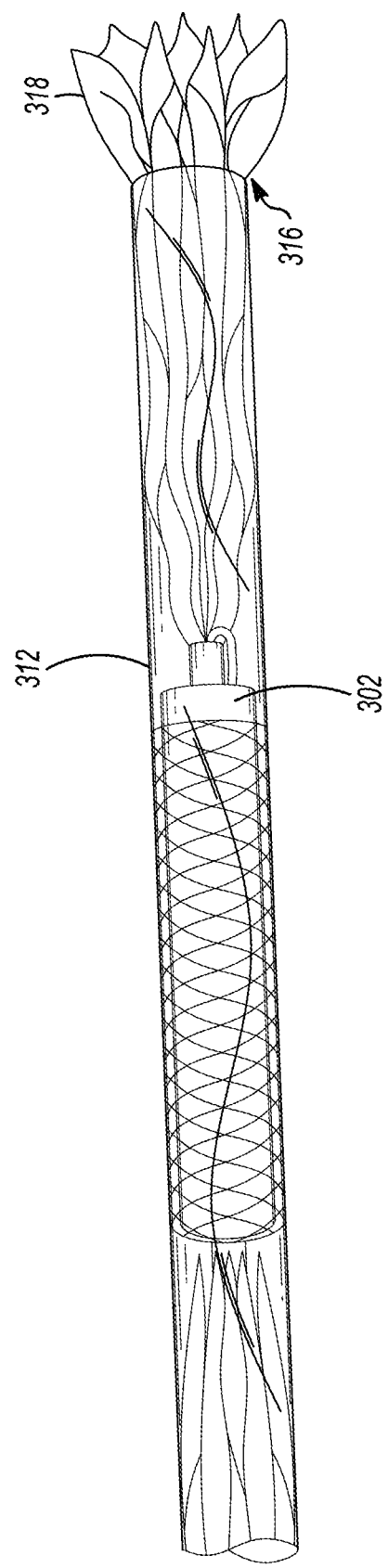
Figure 3D:
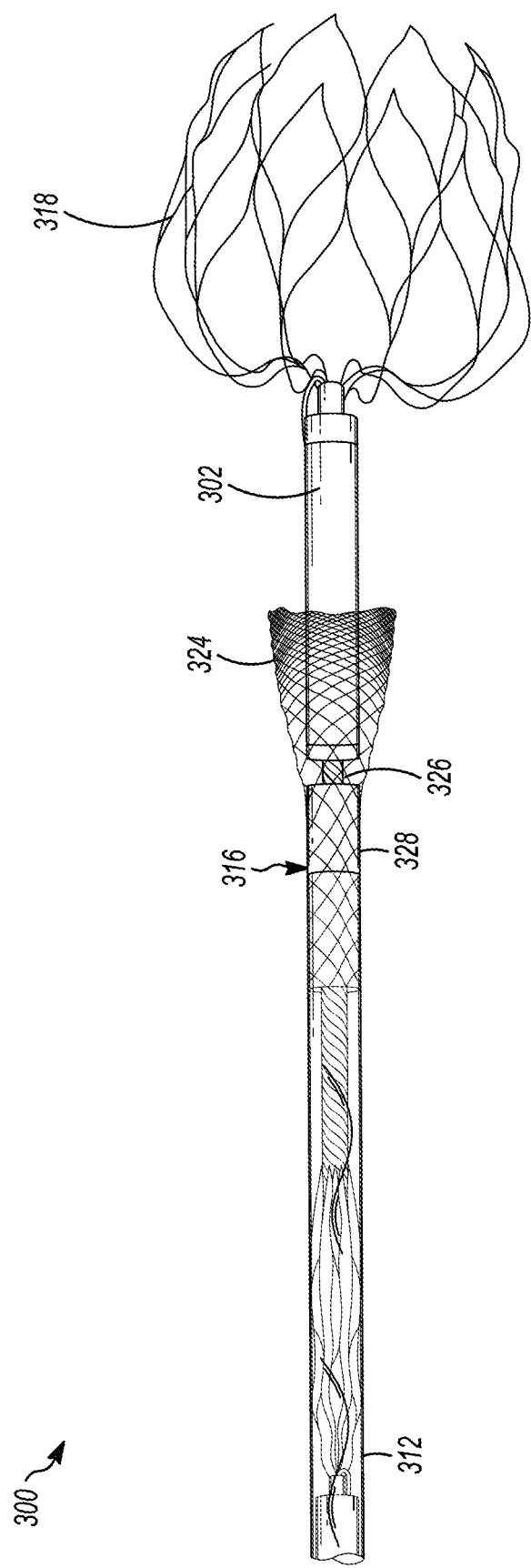

The device 302 can then be pushed through the delivery shaft 312 until it exits the distal end 316 of the delivery sheath 306, as shown in FIG. 3C. Upon exiting the distal end 316 of the delivery sheath 306, the first expandable cage 318 may expand, as shown in FIG. 3D. In embodiments, as is further shown in FIG. 3D, the device 302 may include a mesh skirt 324 at least partially surrounding an inlet 326 of a pump housing 328, and configured to be compressed until the mesh skirt 324 is pushed out of the delivery shaft 312, at which time the mesh skirt 324 may be configured to expand.

The illustrative circulatory support device delivery system 300 shown in FIGS. 3A-3D is not intended to suggest any limitation as to the scope of use or functionality of embodiments of the present disclosure. The illustrative circulatory support device delivery system 300 also should not be interpreted as having any dependency or requirement related to any single component or combination of components illustrated therein. Additionally, various components depicted in FIGS. 3A-3D may be, in embodiments, integrated with various ones of the other components depicted therein (and/or components not illustrated), all of which are considered to be within the ambit of the present disclosure.

Figure 4:
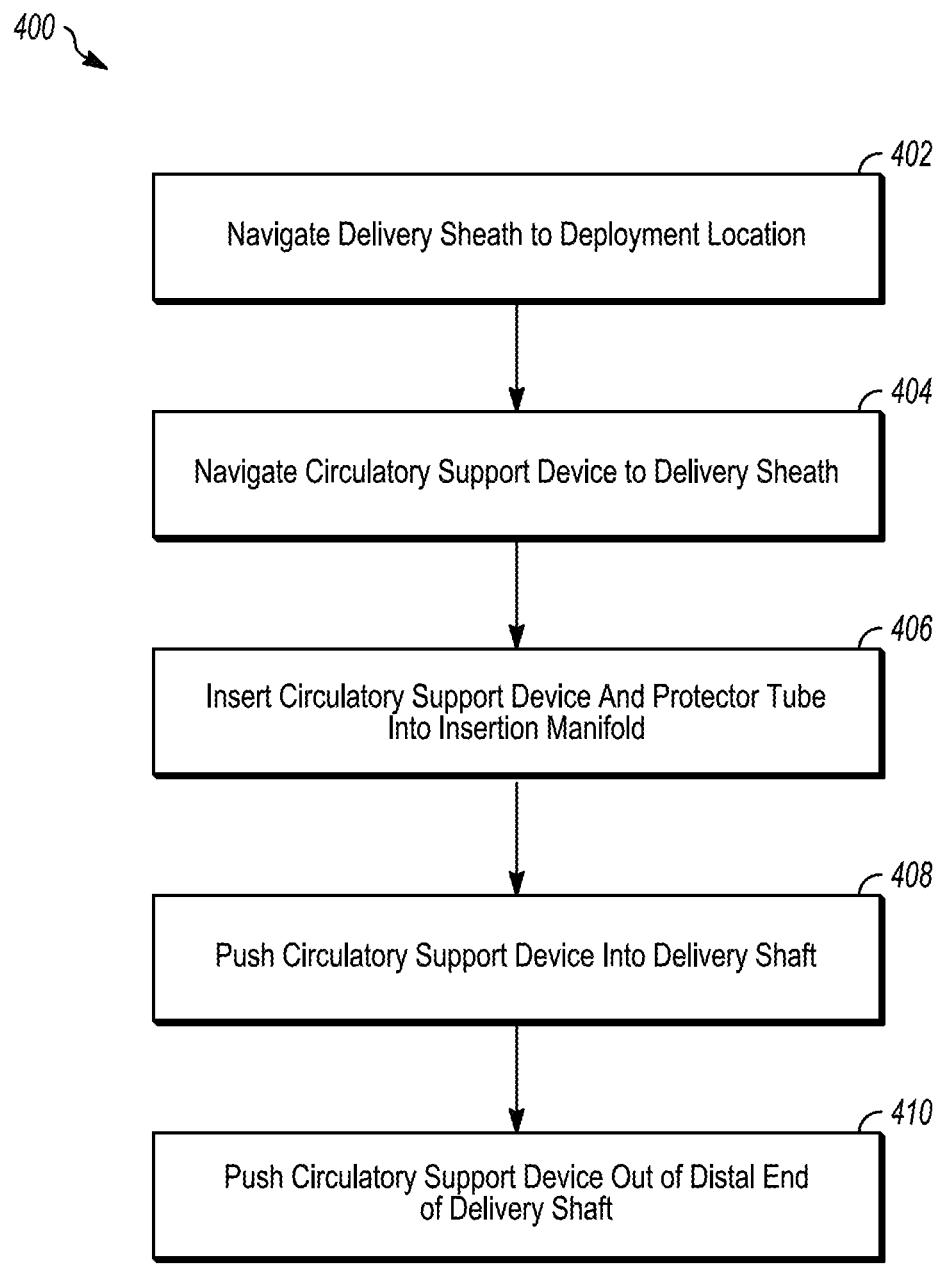
FIG. 4 is a flow diagram depicting an illustrative method of deploying a circulatory support device, in accordance with embodiments of the subject matter disclosed herein.

As described above, with reference to FIGS. 3A-3D, embodiments of the subject matter disclosed herein may facilitate an improved device deployment process. FIG. 4 is a flow diagram depicting an illustrative method 400 of deploying a circulatory support device, in accordance with embodiments of the subject matter disclosed herein. According to embodiments, the circulatory support device may be, or be similar to, the circulatory support device 100 depicted in FIG. 1, the circulatory support device 200 depicted in FIG. 2, and/or the circulatory support device 302 depicted in FIGS. 3A-3D.

That is, for example, embodiments of the circulatory support device may include a flexible cannula having a fluid outlet at a proximal end; and a pump assembly disposed at a distal end of the flexible cannula. The pump assembly may include a pump housing having a fluid inlet defined therein; a motor disposed within a distal end of the housing; and an impeller, driven to rotate by the motor, and configured to push blood toward the fluid outlet. The circulatory support device may further include a helical tube coupled to a proximal end of the pump housing and extending through at least a portion of the flexible cannula, where one or more conductors are disposed within the helical tube. Embodiments of the circulatory support device further include a mesh skirt at least partially surrounding the pump housing, adjacent the fluid inlet; an expandable cage coupled to the distal end of the pump housing; and/or the like.

According to embodiments, the method 400 may facilitate deploying a circulatory support device by positioning the circulatory support device in a deployment location without inserting a guidewire through the circulatory support device. As shown in FIG. 4, embodiments of the method 400 include navigating a delivery sheath to a deployment location following a guidewire (block 402). In embodiments, the delivery sheath includes (1) an insertion manifold having a proximal opening and a distal opening, and (2) a delivery shaft extending from the distal opening. According to embodiments, navigating the delivery sheath to the deployment location includes passing a guidewire through the delivery sheath and tracking at least one of the guidewire and the delivery sheath during navigation. In embodiments, navigating the delivery sheath to the deployment location includes positioning the distal end of the delivery shaft adjacent the cage location.

As is shown, embodiments of the method 400 further include navigating the circulatory support device to the delivery sheath (block 404). In embodiments, during this step, the circulatory support device is disposed within a protector tube. Embodiments of the method 400 further include inserting the circulatory support device and protector tube into the proximal opening of the insertion manifold (block 406). In embodiments, the insertion manifold includes a stop surface disposed therein and configured to engage a distal edge of the protector tube, thereby preventing the protector tube from being pushed into the delivery shaft.

Embodiments of the method 400 further include pushing the circulatory support device into the delivery shaft (block 408). As indicated above, the protector tube may be prevented from entering the delivery shaft by the stop surface. In embodiments, pushing the circulatory support device into the delivery shaft may include pushing on the helical tube. The method 400 may further include pushing the circulatory support device out of a distal end of the delivery shaft (block 410). According to embodiments, upon exiting the delivery shaft, one or more expandable cage may be configured to expand and engage a cage location, thereby securing the circulatory support device in place.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

I claim:

1. A circulatory support device defining a proximal direction and an opposite distal direction, the circulatory support device comprising:

a flexible cannula having a fluid outlet at a proximal end thereof; and a pump assembly disposed at a distal end of the flexible cannula, the pump assembly comprising:
- a pump housing having a fluid inlet defined therein;
- a motor disposed within a distal portion of the housing;
- an impeller, driven to rotate by the motor, and configured to push blood toward the fluid outlet;

a tube coupled to a proximal end of the pump housing and extending through at least a portion of the flexible cannula; and one or more conductors disposed within the tube and being operatively coupled to the motor.

2. The circulatory support device of claim 1, further comprising a mesh skirt at least partially surrounding the pump housing.

3. The circulatory support device of claim 1, further comprising an expandable cage coupled to the distal end of the pump housing.

4. The circulatory support device of claim 1, further comprising an expandable cage coupled to the proximal end of the flexible cannula.

5. The circulatory support device of claim 1, further comprising:
- a first expandable cage coupled to the distal end of the pump housing and configured to be disposed within a left ventricle of a subject; and
- a second expandable cage coupled to the proximal end of the flexible cannula and configured to be disposed within the aorta.

6. The circulatory support device of claim 1, wherein at least a portion of the flexible cannula is configured to be disposed through an aortic valve opening and is configured to be compressible such that the aortic valve can close on the at least the portion of the flexible cannula.

7. The circulatory support device of claim 1, wherein the one or more conductors are configured to operably couple the motor to a control unit and extend from a distal end of the tube, along an outside of the pump housing, and into the distal end of the pump housing.

8. The circulatory support device of claim 1, further comprising:
- a mesh skirt partially surrounding the pump housing; and
- an expandable cage coupled to one of (1) a distal end of the pump housing and configured to be disposed within a left ventricle of a subject, or (2) the proximal end of the flexible cannula and configured to be disposed within an aorta of a subject.

9. A circulatory support device defining a proximal direction and an opposite distal direction, the circulatory support device comprising:
- a flexible cannula having a fluid outlet at a proximal end;
- a pump assembly disposed at a distal end of the flexible cannula, the pump assembly comprising:
  - a pump housing having a fluid inlet defined therein;
  - a motor disposed within a distal portion of the pump housing; and
  - an impeller, driven to rotate by the motor, and configured to push blood toward the fluid outlet;
- a first expandable cage coupled to the distal portion of the pump housing;
- a second expandable cage coupled to the proximal end of the flexible cannula;
- a catheter disposed proximally from the flexible cannula.

10. The circulatory support device of claim 9, further comprising a mesh skirt at least partially surrounding the pump housing.

11. The circulatory support device of claim 9, wherein the fluid inlet is disposed between the flexible cannula and the motor.

12. The circulatory support device of claim 9, wherein the first expandable cage is configured to be disposed in a left ventricle of a subject.

13. The circulatory support device of claim 9, wherein the second expandable cage is configured to be disposed in an aorta of a subject.

14. The circulatory support device of claim 9, further comprising:
- a tube coupled to a proximal end of the pump housing and extending through at least a portion of the flexible cannula; and
- one or more conductors disposed within the tube and being operatively coupled to the motor.

15. The circulatory support device of claim 9, wherein the one or more conductors are configured to operably couple the motor to a control unit and extend from a distal end of the tube, along an outside of the pump housing, and into the distal portion of the pump housing.

16. The circulatory support device of claim 9, wherein at least a portion of the flexible cannula is configured to be disposed through an aortic valve opening and is configured to be compressible such that the aortic valve can close on the at least the portion of the flexible cannula.

* * * * *

UNITED STATES PATENT AND TRADEMARK OFFICE
CERTIFICATE OF CORRECTION

PATENT NO. : 11,484,698 B2  
APPLICATION NO. : 16/720620  
DATED : November 1, 2022  
INVENTOR(S) : Lloyd Radman Page 1 of 1

It is certified that error appears in the above-identified patent and that said Letters Patent is hereby corrected as shown below:

On the Title Page

Related U.S. Application Data (60) Lines 1-2 delete "Provisional application No. 62/872,127 filed Jul. 9, 2019" and insert -- Provisional application No. 62/782,127 filed Dec. 19, 2018 --

Signed and Sealed this  
Seventh Day of February, 2023

Katherine Kelly Vidal  
*Director of the United States Patent and Trademark Office*